United States Patent [19]

Perry et al.

[11] Patent Number: 4,832,039
[45] Date of Patent: May 23, 1989

[54] LINEAR, LOW NOISE INFLATION SYSTEM FOR BLOOD PRESSURE MONITOR

[75] Inventors: William D. Perry; Donald H. Heihn, both of San Antonio, Tex.

[73] Assignee: Nippon Colin Co., Ltd., Komaki, Japan

[21] Appl. No.: 29,072

[22] Filed: Mar. 23, 1987

[51] Int. Cl.⁴ ............................................. A61B 5/02
[52] U.S. Cl. ..................................... 128/680; 128/682
[58] Field of Search ................ 128/672, 677, 680–686; 364/415–417; 417/312, 540–544; 137/565

[56] References Cited

U.S. PATENT DOCUMENTS

| | | | |
|---|---|---|---|
| 4,378,807 | 4/1983 | Peterson et al. | 128/680 X |
| 4,493,326 | 4/1985 | Hill et al. | 128/680 |
| 4,567,899 | 2/1986 | Kamens et al. | 128/680 |
| 4,625,277 | 11/1986 | Pearce et al. | 128/680 X |

4,703,760  11/1987  Miyawaki et al. ................. 128/681

Primary Examiner—Kyle L. Howell
Assistant Examiner—Angela D. Sykes
Attorney, Agent, or Firm—Matthews & Branscomb

[57] ABSTRACT

A compact, low noise inflation system for pressurizing occlusion cuffs used in conjunction with automatic blood pressure monitoring equipment. In the preferred embodiment, an electric pump is controlled by a closed-loop, pressure feedback control circuit which compares the cuff pressure with a desired pressurization profile set by the user or stored in a memory device. Acoustic filters are connected to the intake and exhaust ports of the pump to attenuate the intensity of acoustic noise and pressure waves to allow accurate detection of oscillometric pulse data by the blood pressure monitoring system.

10 Claims, 3 Drawing Sheets

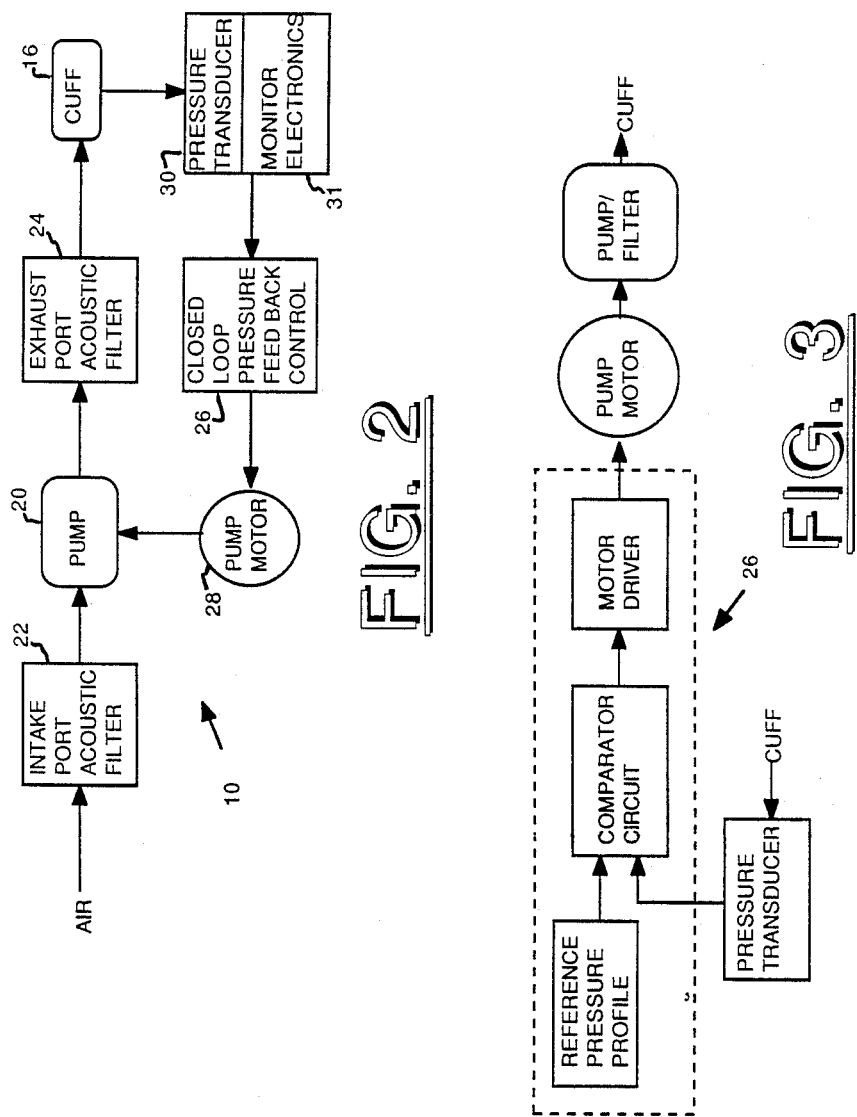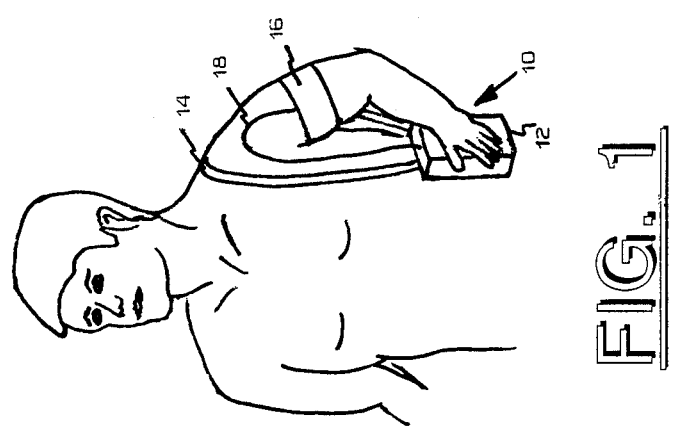

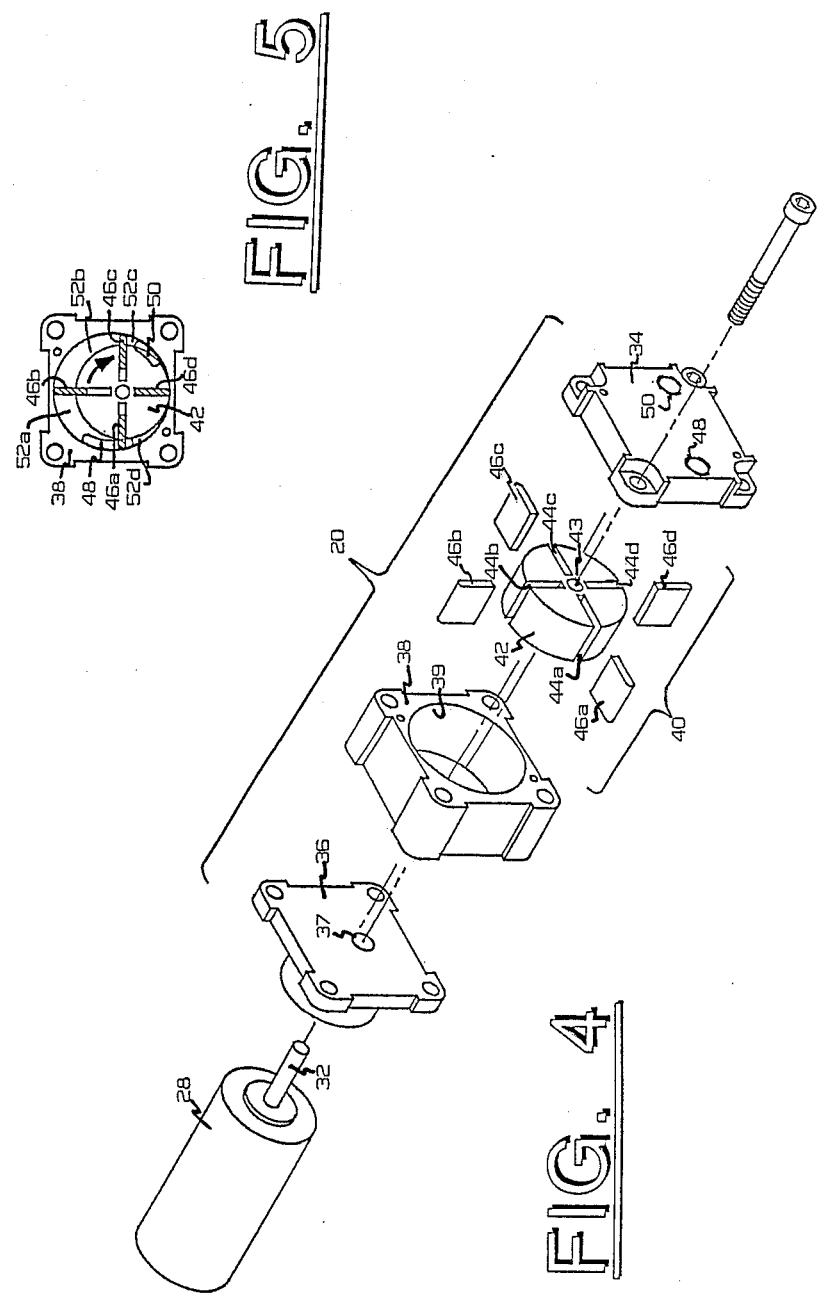

LINEAR, LOW NOISE INFLATION SYSTEM FOR BLOOD PRESSURE MONITOR

FIELD OF THE INVENTION

The present invention relates generally to inflation systems for occlusion cuffs used in connection with blood pressure monitoring systems. In particular, the present invention provides an inflation system for pressurizing an occlusion cuff in accordance with a predetermined pressurization profile, while maintaining a very low level of acoustic noise, thus allowing accurate detection of oscillometric blood pressure pulse data.

BACKGROUND

In many diagnostic situations it is desirable for a doctor to be able to monitor a patient's blood pressure over long periods of time. Numerous blood pressure monitoring systems have been developed to provide automatic measurement of a patient's blood pressure. Many of these automatic monitoring systems are based on oscillometric techniques in which an indirect indication of blood pressure is obtained by measuring pressure variations in a pressurized cuff placed on the patient's arm. Such measurements can be made during either the pressurization or the depressurization of the cuff. The cuff pressurization cycle is commonly referred to as the upramp, while the depressurization cycle is referred to as the downramp.

It is extremely desirable to have a linear pressurization or depressurization curve when using an automatic monitoring system. Linearity of the curve significantly decreases the lenght of time required for measurement and allows the system to make a more accurate measurement. In addition, there are certain advantages in measuring blood pressure on the upramp portion of the cuff pressurization curve. In particular, a system which measures on the upramp avoids the need to inflate the cuff to an unnecessarily high level which can cause discomfort for the patient. For systems making measurement on the upramp portion of the cuff pressurization curve, it is also desirable to have the cuff quickly pressurized to a predetermined level, e.g., 40 millimeters of mercury, to avoid making unnecessary measurements at pressure levels well below those at which systolic and diastolic pressure are expected to occur.

One type of cuff inflation system used for automatic blood pressure monitoring devices employs a source of pressurized gas, such as a conventional carbon dioxide canister. The flow of the pressurized gas can be controlled by appropriate valves and expansion chambers to provide a substantially linear cuff pressurization curve. Another approach to providing a cuff inflation system involves the use of an electric pump which is controlled by a closed-loop, pressure feedback system to obtain the desired inflation profile over the range of pressures which are used for measuring the oscillometric pulses. Although electric pumps can be controlled to produce the desired inflation profile, such pumps produce pressure waves and acoustic noise. The pressure waves propagate through the pneumatic system and interfere with the detection of oscillometric pulse data. The acoustic noise tends to be an annoyance for the user, since the measurement system typically is used over long periods of time.

SUMMARY OF THE INVENTION

The present invention overcomes the difficulties of prior inflation systems by providing a compact, low noise, cuff inflation system which can be controlled to produce the desired cuff pressurization profile. In the preferred embodiment, a sliding vane pump is employed as the inflation source. The operation of the pump is controlled by a closed-loop, pressure feedback control circuit which compares the actual cuff pressure with a desired pressurization profile set by the user or stored in a memory device. If the actual cuff pressurization profile differs from the reference pressurization profile, the control circuit increases or decreases the pump rate to maintain the desired pressurization profile.

Acoustic filters are connected to the intake and the exhaust ports of the pump to reduce the level of undesired pressure waves and acoustic noise. In the preferred embodiment, the acoustic filters each comprise a resonant chamber having a pneumatic nozzle passing therethrough. The pneumatic nozzle has a central longitudinal bore which defines an airflow path for communicating air streams to or from the respective port of the pump. A transverse bore in the nozzle establishes an airflow path between the longitudinal bore and the resonant cavity. The resonant chamber and the above-described bores in the nozzle cooperate to create an acoustic impedance which attenuates the intensity of pulsating pressure waves created by operation of the pump.

BRIEF DESCRIPTION OF THE DRAWINGS

FIG. 1 is an elevated perspective view of a patient wearing a portable blood pressure monitoring system employing the linear, low noise cuff inflation system of the present invention.

FIG. 2 is a schematic block diagram showing the functional elements of the cuff inflation system of the present invention.

FIG. 3 is a schematic block diagram of the closed-loop pressure feedback circuit used to control the inflation pump of the present invention.

FIG. 4 is a partially exploded perspective view of the sliding vane pump of the present invention.

FIG. 5 is a cross-sectional view of the sliding yane pump of the present invention, showing details relating to the sliding vane assembly.

FIG. 7a is a cross-sectional front view of the resonant chambers of the acoustic filter assembly, taken along line 7a—7a of FIG. 6a.

DETAILED DESCRIPTION OF THE PREFERRED EMBODIMENT

Figure 7A:
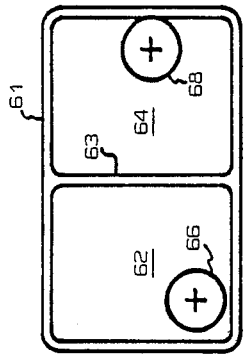

Referring to the drawings in more detail and to FIG. 1 in particular, a blood pressure monitoring system including the linear, low noise cuff inflation system 10 of the present invention is shown being worn by a patient. The inflation system 10 and the monitoring electronics are contained in a compact housing 12 which is supported on the patient by a strap 14. The pressure measurements are made by a pressure transducer that is in fluid communication with a pressurized cuff 16 which is wrapped around the patient's arm in a conventional manner as shown in FIG. 1. A tube assembly, 18 which is routed between the housing 12 and the pressurizable cuff 16, comprises a pneumatic line for providing pressurized gas from the inflation system to the cuff and for communicating the blood pressure signals from the cuff to the transducer contained in the housing. An occlusion cuff 16 used in such an automatic blood pressure monitoring system typically has a volume of approximately 700 cc. In general, it is necessary to inflate the cuff to a pressure of between 200 and 300 millimeters of mercury to obtain the oscillometric pulse data needed to measure the patient's systolic and diastolic blood pressure.

The functional features of the inflation system 10 can be seen by referring to the simplified schematic block diagram shown in FIG. 2. The inflation system 10 comprises a pump 20, which in the preferred embodiment is in the form of a sliding vane pump, described in greater detail below. An intake acoustic filter 22 is attached to the intake port of the pump and an exhaust acoustic filter 24 is attached to the exhaust port to attenuate the noise and vibrations produced by the pump. Operation of the pump 20 is controlled by a closed-loop pressure feedback circuit 26 which controls the pump motor 28 to maintain a desired pressurization profile over the range of pressures needed to obtain the oscillometric data. The pump 20 pressurizes the occlusion cuff 16 which is attached to the patient's arm as described above. As the cuff 16 is inflated, the pressure variations in the cuff are detected by the pressure transducer 30. The pressure measured by the transducer will include a DC component, corresponding to the cuff pressurization profile, and will also contain an AC component related to oscillometric pressure variations in the cuff. The oscillometric pressure variations are filtered from the composite pressure signal and are processed by the blood pressure monitor electronics 31 to obtain an indication of the patient's blood pressure.

A simplified closed-loop pressure feedback circuit of the type employed in the present invention is shown schematically in FIG. 3. The DC component of the output signal of the pressure transducer 30 is fed into a comparator circuit which compares the actual pressurization of the cuff (upramp) to a reference pressurization profile which can be set manually or stored in a conventional memory device. If the actual pressurization of the cuff is different from the reference pressurization profile, the comparator circuit generates an error signal which is used to control the motor driver to increase or decrease the pump rate as needed. Closed-loop pressure feedback circuits, such as that shown in FIG. 3, for controlling the operation of a pump are known in the art and, therefore, the specific components used in the control circuit of the present invention are not shown.

Details relating to the pump assembly of the preferred embodiment can be seen by referring to FIG. 4. The pump assembly comprises an electric motor 28 having a shaft 32 for imparting rotary motion to the rotor of a sliding vane pump assembly 20. The pump assembly 20 includes a housing comprising front and rear endplates 34 and 36, respectively, a central body portion 38, and a sliding vane assembly assembly 40. The central body portion 38 of the housing includes a longitudinal bore 39 to receive the sliding vane rotor assembly 40. The sliding vane rotor assembly 40 comprises a generally cylindrical rotor 42 having transverse slots 44a-44d for receiving sliding vanes 46a-46d, respectively. The pump assembly 20 is attached to the electric motor 28, with the motor shaft 32 received through aperture 37 in endplate 36 and further received in the central aperture 43 of the pump rotor 42. As the rotor 42 is turned by the motor 28, air is received though intake port 48 in endplate 34 and is compressed in chambers defined by adjacent pairs of vanes.

The compression cycle of the pump can be seen by referring to the cross-sectional view of the pump assembly shown in FIG. 5. As can be seen in this view, the central axis of the rotor 42 is offset slightly from the central axis of the longitudinal bore 39 in the central body portion 38 of the pump housing. A pressure chamber is defined between the outer face of the rotor 42 and the inner face of the bore 39 by adjacent vanes, e.g. chamber 52a defined by vanes 46a and 46b. The chamber 52a in the position shown in FIG. 5 is in air flow communication with the intake port 48, shown in phantom. As the chamber 52a rotates in a clockwise direction toward the position occupied by 52b in FIG. 5, the chamber 52a expands and is filled with a quantity of air received through the intake port 48. The rotor continues to rotate in a clockwise direction and is sealed as the vane 46a rotates past the pump intake port 48. As the chamber continues to rotate to the position of chamber 52c in FIG. 5, the air in the chamber is compressed and is eventually exhausted through exhaust port 50.

As was discussed above, it is possible to control the operation of the pump 20 to obtain a cuff pressurization profile which is substantially linear over the range of pressures for which the monitor electronics measures oscillometric data. However, operation of the pump tends to produce pressure waves which propagate through the pneumatic system and interfere with the detection of oscillometric pulse data. The inflation system of the present invention overcomes these difficulties by providing acoustic filtering of the airstreams passing through the intake and exhaust ports of the pump. Attachment of the invention filter assembly 60 to the rotary vane pump assembly can be seen by referring to the exploded isometric view of FIG. 6a and the isometric view of the complete assembly shown in FIG. 6b.

Figure 6A:
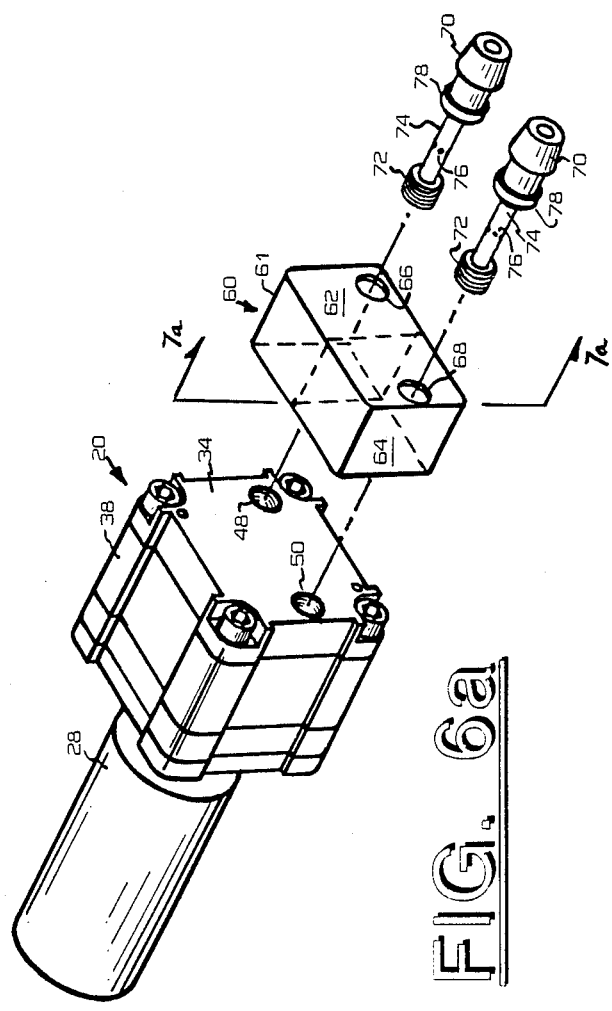
FIG. 6a is an exploded isometric view of the connection of the acoustic filter assembly to the sliding vane pump assembly.
Figure 6B:
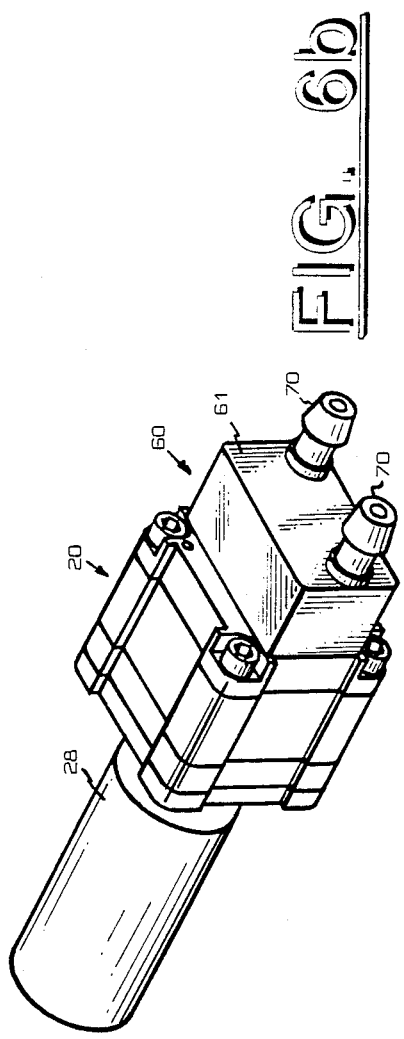
FIG. 6b is a isometric view of the acoustic filter assembly of the present invention attached to the sliding vane pump.

The filter housing 61 comprises intake and exhaust filter cavities 62 and 64, each of which is shown in phantom in FIG. 6A. The chambers 62 and 64 are essentially identical, except for the placement of the apertures 66 and 68 for receiving pneumatic connectors. A pneumatic nozzle 70 is received through each of the apertures 66 and 68 in the filter housing and secured in the in the intake and exhaust ports 48 and 50, respectively, of the pump assembly by threaded connectors 72. Each of the pneumatic nozzles 70 comprises a tubular central body portion 74 having two transverse bores 76 which cooperate with the resonant chambers to reduce the effect of pressure waves, as described in greater detail below. With the filter housing 61 secured to the endplate 34 of the pump assembly as shown in FIG. 6b, the collars 78 on each of the nozzles 70 seal the chambers 62 and 64 to define intake and exhaust resonant cavity filter chambers, corresponding to the intake and exhaust acoustic filters 22 and 24, respectively, shown in FIG. 1.

Figure 7B:
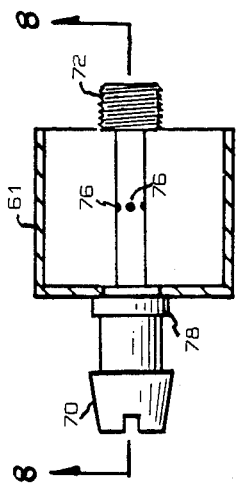
FIG. 7b is a cross-sectional side view of a resonant chamber of the acoustic filter assembly of the present invention.

Details relating to the intake and exhaust filter cavities can be seen by referring to FIGS. 7a and 7b. The wall of the filter housing 61 and the filter cavity partition 63 are formed of metal or plastic having a thickness of 0.031 inch. Each of the filter cavities is approximately 0.494 inches wide, 0.594 inches tall and 0.500 inches deep, thus giving the chamber a volume of 0.147 cubic inches. In the preferred embodiment, the filter housing is formed of brass, although plastic materials, such as Delrin, can also be used.

Figure 8:
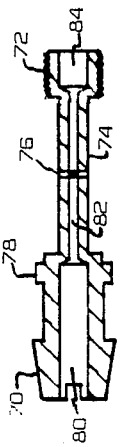
FIG. 8 is a cross-sectional side view of the nozzle shown in FIG. 7b, showing details relating to the air flow path through the nozzle.

The pneumatic nozzle 70 of the preferred embodiment is shown in the cross-sectional view of FIG. 8. The airflow path through the nozzle is defined by longitudinal bores 80, 82, and 84. In the preferred embodiment, the bores 80 and 84 each have a diameter of 0.094 inches, while the central longitudinal bore has a diameter of approximately 0.031 inches. The transverse bores 76 in the central tubular portion each have a diameter of 0.020 inches. In alternate embodiments of the invention filter assembly, the diameter of the central longitudinal bore 82 ranges from 0.031 inches to 0.062 inches. Variation of the diameter of the central orifice 82 affects both the inflation rate of the system and the noise attenuation characteristics of the filter. For example, using the 0.031 inch diameter, the inflation system is capable of pressurizing a 700 cc cuff to a pressure of 200 mm of mercury in approximately 17.5 seconds, while maintaining a noise level of only 31 dB. In the alternate embodiments, the inflation time is decreased and the noise level is increased. For example, in the alternate embodiment for which the diameter of the bore 82 is 0.062 inches, the inflation time is reduced to 8 seconds, while the noise level is increased to 39 dB.

Operation of the above-described filters in conjunction with the intake and exhaust ports of the pump can be understood by a simplified analysis of the reflected noise generated by the flow of air through the nozzles 70 in response to the action of the pump. Although the following discussion is directed to operation of the acoustic filter associated with the intake port 48 of the pump, similar principles apply with respect to the acoustic filter associated with the output port 50. As the pump receives air through the nozzle 70, an average direct current flow of air is established in the air flow channel defined by the longitudinal bores 80, 82 and 84 of the nozzle. Movement of the vanes of the pump past the intake port, however, leads to the production of pressure waves in the air flow channel. This phenomenon causes pulsating or alternating current flows at a number of frequencies which are superimposed on the average direct current air flow through the channel. The pressure waves associated with these alternating current flows tend to propagate through the pneumatic system and interfere with the detection of oscillometric pulse data needed for the measurement of blood pressure. The adverse effect of these alternating current components can be eliminated to an acceptable degree by creating an appropriate acoustical impedance at a point in the air flow path to counteract the effect of the alternating current components. The acoustic impedance created by the acoustic filter of the present invention is a function of three parameters: (1) the diameter of the central longitudinal bore 82; (2) the diameter of the transverse bores 76; and (3) the volume of the resonant chamber 62.

The frequency of the pressure waves created by the pump 20 is a function of the rotary speed of the pump and the number of vanes in the sliding vane assembly 40. In the present invention, the normal operational range of the pump is between 3000 and 6000 revolutions per minute. It has been determined that these operational parameters produce undesirable pulsating pressure waves in the frequency range of approximately 200 to 400 Hz. The acoustic filter having the parameters described in connection with the preferred embodiment has a center frequency of approximately 280 Hz and is exceptionally effective in reducing the pulsating current flows of the pressure waves in the range produced by the pump.

Although the linear, low noise cuff inflation system of the present invention has been described in connection with the preferred embodiment, it is not intended to be limited to the specific form set forth herein, but, on the contrary, it is intended to cover such alternatives and equivalents as can reasonably be included within the spirit and scope of the invention as defined by the appended claims.

We claim:

1. A low noise inflation system for pressurizing an occlusion cuff for use in conjuntion with a blood pressure monitoring system, comprising:
   a pressurization source having an intake port and an exhaust port, said exhaust port being in airflow communication with said occlusion cuff to cause pressurization thereof;
   means for controlling said pressurization source to produce a pressurization profile in said cuff corresponding to a predetermined reference pressurization profile;
   means for attenuating the pressure waves produced by said pressurization source;
   said means for attenuating said pressure waves comprising a first acoustic filter in air flow communication with said exhaust port of said pump;
   said means for attenuating said pressure waves further comprising a second acoustic filter in airflow communication with said intake port of said pump; and
   said first and second acoustic filters comprising resonant cavity filter assemblies, each said filter assembly comprising a resonant cavity and a pneumatic nozzle passing through said cavity, said nozzle having a central longitudinal bore defining an air flow channel for the respective port of said pump, each said nozzle further comprising a transverse bore for communicating air between said longitudinal bore and said resonant cavity.

2. The inflation system according to claim 1, said pressurization source comprising a pump having a sliding vane assembly.

3. The inflation system according to claim 2, said means for controlling said pump comprising a closed-loop pressure feedback circuit.

4. The inflation system according to claim 1, said longitudinal bore having a diameter between 0.031 inches and 0.062 inches.

5. The inflation system according to claim, said resonant cavity having a volume of 0.147 cubic inches.

6. A low noise inflation system for pressurizing an occlusion cuff for use in conjunction with a blood pressure monitoring system, comprising:
   a pressurization source having an intake port and an exhaust port, said exhaust port being in airflow communication with said occlusion cuff to cause pressurization thereof;

means for controlling said pressurization source to produce a pressurization profile in said cuff corresponding to a predetermined reference pressurization profile;

first and second acoustic filters attached to said intake and exhaust ports, respectively, of said pressurization source; and said first and second acoustic filters comprising resonant cavity filter assemblies, each said filter assembly comprising a resonant cavity and a pneumatic nozzle passing through said cavity, said nozzle having a central longitudinal bore defining an air flow channel for the respective port of said pump, each said nozzle further comprising a transverse bore for communication air between said longitudinal bore and said resonant cavity.

7. The inflation system according to claim 6, said pressurization source comprising a pump having a sliding vane rotary assembly, said pump having an operation range of between 3000 and 6000 revolutions per minute, said pump creating pulsatile alternating current pressure waves having a frequency of between 200 and 400 Hertz.

8. The inflation system according to claim 6, said longitudinal bore having a diameter between 0.031 inches and 0.062 inches, said transverse bore having a diameter of 0.002 inches, and said resonant cavity having a volume of 0.147 cubic inches, said longitudinal bore, transverse bore and resonant cavity cooperating to produce an acoustical impedance for attenuating said pulsatile alternating current pressure waves produced by said pump.

9. A low noise inflation system for pressurizating an occlusion cuff for use in conjunction with a blood pressure monitoring system, comprising:

a sliding vane pump assembly having an intake port and an exhaust port, said exhaust port being in airflow communication with said occlusion cuff to cause pressurization thereof, said pump having an operational range of between 3000 and 6000 revolutions per minute, said pump creating pulsatile alternating current pressure waves having a frequency of between 200 and 400 Hertz;

a closed-loop pressure feedback control circuit means for controlling the said pump to produce a pressurization profile in said cuff corresponding to a predetermined reference pressurization profile;

first and second acoustic filters in airflow communication with said intake and exhaust port of said pump for attenuating said alternating current pressure waves produced by said pump, said first and second acoustic filters comprising resonant cavity filter assemblies, each said filter assembly comprising a resonant chamber and a pneumatic nozzle passing through said chamber, said nozzle having a central longitudinal bore defining an air flow channel for the respective port of said pump, each said nozzle further comprising a transverse bore for communicating air between said longitudinal bore and said resonant chamber.

10. The inflation system according to claim 7, said longitudinal bore having a diameter of 0.031 inches, said transverse bore having a diameter of 0.020 inches, said resonant chamber having volume of 0.147 cubic inches, said resonant chamber cooperating with said longitudinal bore and said transverse bore to create an acoustic impedance for attenuating said alternating current pressure waves produced by said pump, said filter having a center frequency of approximately 280 hertz.

* * * * *